(12) United States Patent
Requardt et al.

(10) Patent No.: US 10,226,644 B2
(45) Date of Patent: Mar. 12, 2019

(54) METHOD FOR PLANNING IRRADIATION OF A PATIENT FOR RADIATION THERAPY

(71) Applicant: Siemens Healthcare GmbH, Erlangen (DE)

(72) Inventors: Martin Requardt, Nuremberg (DE); Bernd Schweizer, Ketsch (DE); David Grodzki, Erlangen (DE); Arne Hengerer, Moehrendorf (DE); Michael Kaus, Nuremberg (DE); Elena Nioutsikou, Erlangen (DE); Sebastian Schmidt, Weisendorf (DE)

(73) Assignee: Siemens Healthcare GmbH, Erlangen (DE)

( * ) Notice: Subject to any disclaimer, the term of this patent is extended or adjusted under 35 U.S.C. 154(b) by 93 days.

(21) Appl. No.: 15/405,748

(22) Filed: Jan. 13, 2017

(65) Prior Publication Data

US 2017/0203123 A1 Jul. 20, 2017

(30) Foreign Application Priority Data

Jan. 15, 2016 (DE) .......................... 10 2016 200 433

(51) Int. Cl.
    *A61N 5/10*      (2006.01)
    *G06T 7/00*      (2017.01)
    *G06F 19/00*      (2018.01)

(52) U.S. Cl.
    CPC .......... *A61N 5/1037* (2013.01); *A61N 5/1039* (2013.01); *G06F 19/3481* (2013.01);
(Continued)

(58) Field of Classification Search
CPC .......... A61N 5/1049; A61N 2005/1061; A61N 5/1038; A61N 5/1065; A61N 5/1069; A61N 5/1067; A61N 5/1042; A61N 5/1064; A61N 2005/1058; A61N 5/103; A61N 5/1039; A61N 5/1045; A61N 2005/1055; A61N 5/107; A61N 2005/1054; A61N 2005/1062; A61N 5/1037; A61N 5/1048;
(Continued)

(56) References Cited

U.S. PATENT DOCUMENTS

| | | | | |
|---|---|---|---|---|
| 7,643,661 | B2* | 1/2010 | Ruchala | A61N 5/103 382/128 |
| 9,922,421 | B1* | 3/2018 | Degani | G06T 7/11 |
| 2002/0025017 | A1* | 2/2002 | Stergiopoulos | G06T 5/50 378/8 |
| 2003/0007601 | A1* | 1/2003 | Jaffray | A61B 6/032 378/65 |

(Continued)

OTHER PUBLICATIONS

Bernatowicz et al., "4D-MRI: Future of Radiotherapy of Moving Targets?," Magnetom Flash Feb. 2015, www.siemens.com/magnetom-world (2015).

*Primary Examiner* — Aklilu K Woldemariam
(74) *Attorney, Agent, or Firm* — Schiff Hardin LLP (57) ABSTRACT

In a method and system for planning irradiation of a patient for therapy, a first time series acquired from computed tomography scan data of the patient is provided to a processor, as is a second time series acquired from magnetic resonance scan data of the patient. A first parameter that characterizes the first time series is acquired, as is a second parameter that characterizes the second time series. The first time series and the second time series are combined in the processor using the first parameter and the second parameter. An irradiation plan is calculated in the processor using the combined first time series and second time series.

10 Claims, 3 Drawing Sheets

(52) U.S. Cl.
CPC .............. *G06T 7/0012* (2013.01); *G06T 7/97* (2017.01); *G06T 2207/10081* (2013.01); *G06T 2207/10088* (2013.01)

(58) Field of Classification Search
CPC .......... A61N 2005/1057; A61N 5/1068; A61B 5/7289; A61B 2034/2055; A61B 34/30; A61B 5/7285; A61B 6/541; A61B 8/08; A61B 6/583; A61B 2090/371; A61B 2090/373; A61B 5/0035; A61B 5/0059; A61B 5/055; A61B 5/704; A61B 6/032; A61B 6/037; A61B 6/4417; A61B 6/482; A61B 6/484; A61B 6/485; A61B 6/507; A61B 6/50; A61B 6/00; A61B 2576/00; A61B 34/10; A61B 6/027; A61B 8/4416; A61B 8/5261; G21K 1/046; G21K 5/10; G06T 2207/10081; G06T 2207/20081; G06T 7/97; G06T 2207/10088; G06T 2207/10116; G06T 2207/20096; G06T 2207/30096; G06T 7/33; G06T 7/337; G06T 7/0012; G06F 17/3028; G06F 19/3481; G01R 33/4812; G06K 9/6256; G06K 9/66; G06N 99/005
USPC .... 382/128, 129, 130, 131, 132; 600/1, 302, 600/437, 439
See application file for complete search history.

(56) References Cited

U.S. PATENT DOCUMENTS

| | | | |
|---|---|---|---|
| 2004/0081269 A1* | 4/2004 | Pan | A61B 6/032 378/4 |
| 2006/0241443 A1* | 10/2006 | Whitmore, III | A61B 8/08 600/439 |
| 2007/0076846 A1* | 4/2007 | Ruchala | A61N 5/103 378/65 |
| 2007/0201613 A1* | 8/2007 | Lu | A61N 5/1049 378/65 |
| 2007/0238951 A1 | 10/2007 | Ferenczi et al. | |
| 2009/0110256 A1* | 4/2009 | Thielemans | A61B 6/032 382/131 |
| 2010/0119032 A1* | 5/2010 | Yan | A61N 5/1049 378/4 |
| 2011/0317896 A1* | 12/2011 | Huber | A61N 5/103 382/131 |
| 2012/0238795 A1* | 9/2012 | Bert | A61N 5/1043 600/1 |
| 2013/0304446 A1* | 11/2013 | Rabinovitz | G06F 19/12 703/11 |
| 2014/0107390 A1* | 4/2014 | Brown | A61N 5/1045 600/1 |
| 2016/0174919 A1* | 6/2016 | Ahn | G01T 1/1603 382/131 |

* cited by examiner

METHOD FOR PLANNING IRRADIATION OF A PATIENT FOR RADIATION THERAPY

BACKGROUND OF THE INVENTION

Field of the Invention

The invention concerns a method for planning irradiation of a patient for radiation therapy, as well as an irradiation planning computer and a non-transitory, computer-readable data storage medium encoded with programming instructions for implementing such a method.

Description of the Prior Art

In radiation therapy, target tissue, for example a tumor, of a patient is irradiated with ionizing radiation. External radiation therapy, wherein irradiation of the body of the patient originates from outside of the body, is known in this connection. Internal radiation therapy, also called brachytherapy, is likewise known. In brachytherapy, radiation sources, which include radioactive substances, are introduced into the body of the patient to locally damage or destroy target tissue in the body of the patient.

It is known to plan and/or monitor irradiation of a patient with the use of imaging. An irradiation plan is conventionally created for this purpose with the use of medical scan data of the patient, created using a three-dimensional imaging method. Computed tomography scan data (CT scan data) are conventionally used for this purpose. Using the CT scan data, firstly the target volume of the irradiation can be defined, and, secondly, surrounding tissue that is to be spared—for example nerve tissue—is localized. Furthermore, the intensity values of the image voxels of the scan data (measured in what are known as "Hounsfield Units") map an electron density at the corresponding location in the body of the patient in a good approximation since the intensity values of the image voxels are based on absorption of the X-ray radiation at the associated locations. In this way the CT scan data can be converted particularly easily into an electron density map for irradiation planning. Since the intensity of the interaction of the radiation correlates with the electron density in the body in the case of irradiation, the attenuation of the radiation as it passes through the body can be calculated easily from the CT scan data. It is due to this property that previously CT scan data has preferably been used when creating an irradiation plan.

However, there is a need to use other imaging methods in irradiation planning that have better soft tissue contrast in order to enable improved identification of target organs and/or organs at risk. One imaging method of this kind, which satisfies the requirement for better soft tissue contrast, is magnetic resonance imaging (MR imaging) by the use of a magnetic resonance device. With imaging of this kind the contrast depends on the distribution of the spin density, the interaction of the spins among each other and/or with their surroundings. A soft tissue contrast can be achieved with MR imaging that is significantly superior to the contrast that can be achieved with a computed tomography device. Furthermore, functional contrasts, for example a diffusion contrast, can also be advantageously recorded with magnetic resonance imaging for irradiation planning.

SUMMARY OF THE INVENTION

An object of the invention is to enable improved planning of irradiation of a patient for radiation therapy.

The inventive method for planning irradiation of a patient has the following method steps:

acquiring a first time series from computed tomography scan data of the patient, acquiring a second time series from magnetic resonance scan data of the patient, acquiring a first parameter which characterizes the first time series, acquiring a second parameter which characterizes the second time series, combining the first time series and the second time series in a processor using the first parameter and second parameter, and calculating an irradiation plan using the combined first time series and second time series and making the irradiation plan available from the processor in electronic form.

Acquiring the first time series of the computed tomography scan data can be recording the first time series by operation of a computed tomography device, or loading a time series, which has already been recorded, from a database into the processor. Acquiring the second time series of the magnetic resonance scan data can be recording the second time series by operation of a magnetic resonance device or loading a time series, which has already been recorded, from a database into the processor. The calculated irradiation plan emitted in an electronic form can be used to control irradiation of the patient. For this purpose, the calculated irradiation plan can be transferred to an irradiation unit, for example a linear accelerator or a brachytherapy unit, for carrying out the irradiation. Furthermore, the calculated irradiation plan can also be stored in a database for subsequent retrieval.

The computed tomography scan data and the magnetic resonance scan data are acquired from a planning volume that is localized in the patient. The planning volume includes the target volume of the irradiation and at least one at-at-risk volume for the irradiation. The planning volume is therefore typically chosen to be so large that the target volume and the at least one at-risk volume are contained in the planning volume in each case. The target volume includes the target structures in the body of the patient that are to be irradiated by the radiation therapy. The target tissue is typically localized in the target volume. The target volume is typically separated from the at least one at-risk volume. The at least one at-risk volume includes at-risk tissue for the irradiation.

In the calculation of the irradiation plan the target volume and/or the at least one at-risk volume can be marked semi-automatically or manually, for example by marking a point or a 2D or 3D Region-of-Interest (ROI) in the computed tomography scan data and/or magnetic resonance scan data acquired by the planning volume. A radiation dose can then be allocated to the target volume in irradiation planning. A maximum dose or a maximum volume dose can be allocated to the at least one at-risk volume in irradiation planning, and this dose must not be exceeded during radiation therapy.

The first time series of the computed tomography scan data includes a number of three-dimensional computed tomography image data sets that are acquired at different times. In this way the first time series of the computed tomography scan data can form a four-dimensional image data set. The four dimensions are composed of the three spatial dimensions and one time dimension. The first time series of the computed tomography scan data can in this way also be called a 4D computed tomography image data set. The first time series of the computed tomography scan data can be acquired over a number of respiratory cycles of the patient. The three-dimensional image data sets acquired over the number of respiratory cycles can then be grouped to form the respective respiratory phases, so reconstruction of image data sets that correspond to one respiratory phase respectively is possible.

Accordingly, the second time series of the magnetic resonance scan data can be acquired by operation of the magnetic resonance device. Magnetic resonance devices, like computed tomography devices, are suitable for 4D scans. The second time series of the magnetic resonance scan data can also be acquired over a number of respiratory cycles of the patient.

The fact that the computed tomography scan data and magnetic resonance scan data are acquired for the irradiation planning in a time-resolved manner provides the advantage that a movement of the patient, in particular a respiratory movement, can be taken into account in irradiation planning. Therefore, a movement of the target volume and/or of the at least one at-risk volume can be taken into account in irradiation planning. This can be important if irradiation is to be performed in the vicinity of an organ, such as the liver or lungs, which moves a great deal with respiration.

The first parameter can be derived from the computed tomography scan data of the first time series. The first parameter can then be obtained by a computing algorithm, which has the computed tomography scan data of the first time series as the input parameter. Alternatively or additionally, the first parameter can also be recorded in addition to the computed tomography scan data during acquisition of the first time series, for example by an external device or accessory device of the computed tomography device.

The second parameter can also be calculated from the magnetic resonance scan data of the second time series and/or be recorded in addition to the magnetic resonance scan data during acquisition of the second time series. Of course, acquiring of more than one first parameter and/or more than one second parameter is also conceivable. The second parameter can be different from the first parameter.

The first parameter can describe a course over time of the movement of the patient during acquisition of the first time series. In particular, the first parameter can characterize a course over time of a respiratory movement of the patient during acquisition of the first time series. Therefore the first parameter can describe a movement phase and/or a movement amplitude or a course over time of the movement phase and/or movement amplitude of the patient during acquisition of the first time series. Therefore the first parameter can characterize, for example, the respiratory phase and/or the respiratory amplitude during acquisition of the first time series. Furthermore, the first parameter can also describe a deformation of tissue regions of the patient that occurs due to a movement of the patient during acquisition of the first time series. In certain cases it is also conceivable that instead of or in addition to the respiratory movement, a different movement of the patient, for example a cardiac movement or a random movement, is characterized by means of the first parameter.

The second parameter can also describe a course over time of the movement of the patient during acquisition of the second time series. The explanations of the preceding paragraph relating to the first parameter apply analogously to the second parameter.

The first time series and second time series can be combined by execution of a combining algorithm that has the first time series, the second time series, the first parameter and the second parameter as input parameters. The combining algorithm can then have the combined first time series and second time series as an output parameter. Combining of the first time series and second time series can involve an adjustment of the second time series to the first time series or an adjustment of the first time series to the second time series. Of course both time series can also be adjusted during combining.

The first parameter and second parameter can constitute a basis for combining the first time series and second time series. The first time series and second time series are therefore combined not just using the direct image contents of the computed tomography scan data and magnetic resonance scan data, but also by taking into account the first parameter and the second parameter. However, as mentioned, the first parameter and the second parameter can have been derived directly from the image contents of the computed tomography scan data and magnetic resonance scan data. The first parameter and the second parameter can supply valuable additional information which can enable or improve combining of the first time series and second time series.

In an embodiment, first a connection between the first parameter and the second parameter can be determined for combining the first time series and the second time series. The first time series and the second time series can then be combined using the connection determined between the first parameter and the second parameter. For example, combining the first time series and the second time series can be an allocation of the respiratory phase present during acquisition of the first time series, which can be determined using the first parameter, to the respiratory phase present during acquisition of the second time series, which can be determined using the second parameter.

As described in more detail below, combining the first time series and the second time series can be a new arrangement of individual images of the first time series and second time series using the first parameter and the second parameter. For example, by using the first parameter and the second parameter the computed tomography scan data and/or the magnetic resonance scan data can be sorted into individual data sets which each map an identical movement phase and/or movement situation of the patient. These individual data sets can then be reconstructed to form image data that can be used for the calculation of the irradiation plan.

The inventive procedure is based on the consideration that the combined use of 4D computed tomography scan data and 4D magnetic resonance scan data can provide advantages in irradiation planning. For the combined use of the scan data of the two modalities acquired in time series, it is necessary, that both time series correspond with each other. The correspondence of the first time series of the computed tomography scan data and the second time series of the magnetic resonance scan data does not typically exist from the outset. For example, movement phases of the patient, such as respiratory phases, can be designed or arranged differently during acquisition of the first time series and the second time series. Different acquisition times can also exist for the acquisition of the first time series and second time series. A further factor can be a certain time interval, for example of hours or days, between the acquisition of the first time series and the second time series. Furthermore, different devices are typically available in computed tomography imaging for acquiring the respiratory phase of the patient than in magnetic resonance imaging. Discrepancies between the first time series and the second time series can lead to problems in irradiation planning, for example in the contouring.

With the described inventive the first time series of the computed tomography scan data can advantageously be temporally and/or spatially connected to the second time series of the magnetic resonance scan data. In this way irradiation planning based on the combination of the computed tomography scan data and the magnetic resonance scan data can be enabled particularly advantageously.

In another embodiment, the first time series and the second time series includes a synchronization of the first time series and second time series over a movement cycle of the patient.

For this purpose, the first parameter can supply a first item of synchronization information for the computed tomography scan data and the second parameter a second item of synchronization information for the magnetic resonance scan data. The first item of synchronization information and the second item of synchronization information can then be used for synchronization of the first time series and the second time series over the movement cycle of the patient.

The synchronization of the first time series and the second time series can be implemented by the first time series being temporally connected to the second time series. The synchronized first time series and second time series can therefore present the same progress of a cyclical movement of the patient, for example the respiratory movement. A respiratory curve present during the first time series and/or the second time series can be compressed or expanded for the synchronization of the first time series and the second time series.

The synchronized first time series and second time series can be used particularly advantageously in irradiation planning. For example, contours, which are set to a time series during irradiation planning, can be transferred particularly easily to the other time series after synchronization of the two time series and be guided by the movement cycle of the patient. A time-resolved calculation of a dose distribution using the synchronized first time series and second time series is also conceivable in irradiation planning. Those skilled in the art can of course use further expedient possible applications of the synchronized first time series and second time series.

In another embodiment, the synchronization of the first time series and the second time series includes an adjustment of a temporal arrangement of individual images of the first time series and/or second time series, and the calculation of the irradiation plan includes the use of the adjusted temporal arrangement of the individual images of the first time series and/or second time series.

The individual image of the first time series can be a three-dimensional computed tomography data set, which is acquired at a time within the first time series. An individual image of the second time series is equally, in particular, a three-dimensional magnetic resonance data set which is acquired at a time within the second time series. The first time series and the second time series are therefore each composed of a number of successive individual images.

Before synchronization the first time series has a first temporal arrangement of first individual images and the second time series a second temporal arrangement of second individual images. A temporal arrangement of individual images is a sequence of individual images, with a time stamp is associated with each individual image of the sequence of individual images. The time stamp can be defined by the time of acquisition of the individual image within the temporal arrangement of the individual images.

The synchronization of the first time series and the second time series then includes an adjustment of the first temporal arrangement of the first individual images to the second temporal arrangement of the second individual images or vice versa. The adjustment of the temporal arrangement is carried out using the first parameter and the second parameter. Both temporal arrangements of the individual images can also be adjusted. The adjustment of the temporal arrangement of the individual images includes a rearrangement and/or change in the sequence of the individual images. The adjustment of the temporal arrangement of the individual images can include a change in a time stamp of at least one individual image of the temporal arrangement of the individual images.

The adjustment of the temporal arrangement of the individual images of the first time series and/or the second time series constitutes a particularly advantageous possibility for synchronization of the first time series and the second time series.

In another embodiment, acquisition of the first parameter includes use of at least one of the following elements during acquisition of the time series of the computed tomography scan data: a respiratory belt placed on the patient, an optical camera, a spirometer, a radio-frequency-based movement detector, a marking element arranged with the patient.

Of course a combination of elements or techniques that is considered expedient to those skilled in the art can also be used for acquiring the first parameter. By the use of the proposed elements a movement of the patient, in particular a respiratory movement, can be advantageously recorded during acquisition of the first time series of the computed tomography scan data. The signals recorded by the aforementioned elements during acquisition of the first time series can advantageously be stored as first parameters and then be used when combining the first time series and second time series.

The signals recorded by the respiratory belt and/or spirometer during acquisition of the first time series can be used to follow a respiratory movement of the patient during acquisition of the first time series. The spirometer, also called automatic breathing control (ABC), can determine a volume of inhaled or exhaled air to determine the phase of a respiratory cycle of the patient. The optical camera can track an external contour of the patient during acquisition of the first time series and in this way in particular a respiratory movement, but potentially also random movements, of the patient during acquisition of the first time series. For this the optical camera can be installed outside of a bore opening of the computed tomography device and record optical scan data of the patient during the computed tomography scan. The radio-frequency-based movement detection can comprise the use of a radio-frequency sensor or a radio-frequency transceiver module. The marking element can be placed on the patient, for example on a sternum of the patient. The movement of the marking element due to the movement of the patient during acquisition of the first time series can then be identified by means of an optical camera and/or in the computed tomography scan data. The marking element, which can also be called fiducial, can alternatively also be implanted in the patient.

In an embodiment, the acquisition of the second parameter includes use of at least one of the following elements during acquisition of the time series of the magnetic resonance scan data: a magnetic resonance navigator scan, which takes place at the same time as acquisition of the magnetic resonance scan data, a respiratory belt placed on the patient, a spirometer, a marking element arranged with the patient.

Of course a combination of elements or techniques that seems expedient to those skilled in the art for acquiring the second parameter can also be used. By the use of the aforementioned elements a movement of the patient, in particular a respiratory movement, can be recorded during acquisition of the second time series of the magnetic resonance scan data. The signals recorded by the aforementioned elements during acquisition of the second time series can advantageously be stored as the second parameter and then be used during combining of the first time series and second time series.

The magnetic resonance navigator scan can be regarded as part of the magnetic resonance sequence that is used for acquiring the second time series from magnetic resonance scan data. Magnetic resonance navigator scans are known to those skilled in the art, so their mode of operation need not be discussed in more detail herein. A movement of an anatomical structure due to the movement of the patient, in particular the respiratory movement, can be tracked in the magnetic resonance navigator scan. The anatomical structure can be, for example, the diaphragm or the front chest wall of the patient. A one-dimensional pencil beam navigator can particularly advantageously be used in the case of the magnetic resonance navigator scan. It is also conceivable for two navigators to be acquired in a test scan through different anatomical structures of the patient, for example through the diaphragm and through the front chest wall, before acquisition of the second time series. A correlation of the two navigators can then be determined, so during acquisition of the second time series an acquisition of just one navigator is enough to determine the navigator signals in respect of the two anatomical structures by way of calculation.

The use of the respiratory belt and/or spirometer can also supply valuable information about a respiratory movement of the patient during acquisition of the second time series of the magnetic resonance scan data.

Just as in computed tomography imaging, the use of the marking element arranged with the patient can also be expedient in magnetic resonance imaging for detection of a path of movement of the patient. The marking element can then particularly advantageously be detected in the magnetic resonance scan data acquired in the second time series. A dedicated marking element for the magnetic resonance image data, which can be seen in conventional magnetic resonance sequences, can be used for this. It is also conceivable for the same marking element to be arranged with the patient in both computed tomography imaging and magnetic resonance imaging. It can then be expedient to use a dedicated magnetic resonance sequence, which typically supplies a non-clinical contrast, for detection of the marking element in the magnetic resonance scan data. A dedicated magnetic resonance sequence of this kind can use, for example, ultra-short echo times.

In another embodiment, acquisition of the first parameter comprises determining a first vector field map from the first time series and acquisition of the second parameter comprises determining a second vector field map from the second time series, wherein the first time series and the second time series are combined using the first vector field map and the second vector field map.

The first vector field map, also called first vector map, is determined from the computed tomography scan data acquired during the first time series. The first vector field map can be determined by execution of a determining algorithm which has the computed tomography scan data acquired during the first time series as the input parameter and the first vector field map as the output parameter. The first vector field map can then be used as the first parameter for combining the first time series and second time series.

Equally, the second vector field map, also called the second vector map, is determined from the magnetic resonance scan data acquired during the second time series and can then be used as the second parameter for combining the first time series and second time series.

The first vector field map can be designed as a function of time or so as to be time-resolved. The first vector field map accordingly has a number of spatial points at a specific time, with one vector being stored for each spatial point. The vector stored for each spatial point of the first vector field map can characterize a movement of an image content of the computed tomography scan data during the specific time of the first time series for the respective spatial point. The first vector field map can therefore be stored for different times, so the movement of the image content of the computed tomography scan data can be characterized at different times during acquisition of the first time series by means of the first vector field map. The second vector field map can be designed analogously to the first vector field map as a function of time and characterize the movement of the image contents of the magnetic resonance scan data during acquisition of the second time series.

The first vector field map can describe a movement or deformation of tissue regions of the patient during the acquisition of the first time series, caused by the movement of the patient, in particular by the respiratory cycle of the patient. Alternatively, the second vector field map can describe a movement or deformation of tissue regions of the patient during the acquisition of the second time series, caused by the movement of the patient, in particular by the respiratory cycle of the patient.

The first time series and second time series can be combined by combining information which is obtained from combining of the first vector field map and the second vector field map. In this way the first vector field map and the second vector field map can be combined in a first step, for example by registering or fusion, wherein combining information, for example registering parameters or fusion parameters, is obtained. The combining information can then be used as the input parameter for the combining algorithm which combines the first time series and the second time series. Therefore the data sets of the first time series and second time series can be synchronized using the combining information obtained from combining of the first vector field map and second vector field map.

For combining the time series, the calculation of the vector field maps from the time series provides the advantage that the vector field maps can characterize the respective movements in the image contents of the time series especially well. In the first vector field map, those body regions of the patient are highlighted for which there is a particularly pronounced movement of the patient, for example in a respiratory cycle, during acquisition of the first time series. Alternatively, those body regions of the patient are highlighted in the second vector field map for which there is a particularly pronounced movement of the patient, for example in a respiratory cycle, during acquisition of the second time series. The movement-critical body regions that are highlighted in the respective vector field maps can then be merged particularly easily for combining of the first time series and the second time series. In this way it is easily possible, by use of the first vector field map as the first parameter and by use of the second vector field map as the second parameter, to obtain matching movement curves, such as respiratory curves, for the first time series and the second time series.

In another embodiment, the first time series and the second time series are combined by merging the first vector field map and the second vector field map over time.

A time change of the vectors in the first vector field map can be matched to a time change of the vectors in the second vector field map for merging the first vector field map and the second vector field map over time. In this way the first time series and the second time series can be combined in terms of time using the merged first vector field map and second vector field map. The first vector field map and second vector field map already described can be temporally synchronized in this way. The first vector field map and the second vector field map can therefore enable a fusion of the first time series and second time series according to the criterion of a movement of the patient, particularly in the respiratory cycle. The vector field maps can be merged in addition to the use of a further parameter. For example, the respiratory signals measured by means of the respiratory belt can be synchronized between the first time series and second time series using the merging of the first vector field map and second vector field map.

In another embodiment, the first time series and the second time series are combined by registering the first vector field map and the second vector field map over the space.

For example, non-rigid or rigid registering of the first vector field map and second vector field map is conceivable. Using the deformation field obtained from registering, the first time series and the second time series can then be spatially combined. It is possible for the first vector field map and the second vector field map to be registered over space and for the first vector field map and the second vector field map to be merged over time.

In another embodiment, the first time series and the second time series are also combined using a rule which describes a phase shift between the first parameter and the second parameter.

For combining the first time series and second time series, the rule can be loaded from a database in which the rule is stored. The rule can also be created in advance using the acquired first parameter and second parameter. Therefore the rule can be created, for example, using the first vector field map and the second vector field map, with the phase shift between the first vector field map and second vector field map being determined.

The phase shift between the first parameter and the second parameter can be designed as a phase shift in a respiratory curve of the patient. The phase shift can be based, for example, on the fact that a respiratory movement of different organ structures of the patient is acquired in the first parameter and in the second parameter. In this way the phase shift between the first parameter and the second parameter can be based on a use of different techniques for acquiring the first parameter and second parameter.

The phase shift between the first parameter and the second parameter can be known and be stored as a rule in the database. In this way the rule can describe a phase shift of a respiratory curve, which is characterized by the first parameter and/or second parameter, in order to implement a specific number of degrees. Use of the rule can therefore enable improved combining of the first time series and second time series.

In another embodiment, the combined first time series and second time series are used in a calculation of a dose distribution for the calculation of the irradiation plan.

For the calculation of the dose distribution a dose distribution calculation algorithm can be used that has the combined first time series and second time series and irradiation parameters as the input parameters and the calculated dose distribution as the output parameter. Calculation of the dose distribution can also include a simulation of a radiation dose applied during irradiation of the target volume and/or at least an at-risk volume. For this a contour of the target volume and/or the at least one at-risk volume marked in a data set of the first time series and/or second time series can be propagated onto another respiratory phase of the first time series and/or second time series. A particularly accurate dose distribution can be used for the calculation of the irradiation plan due to the simultaneous consideration of time-resolved computed tomography scan data and magnetic resonance scan data.

In another embodiment, a presentation of a course over time of the combined first time series and second time series is displayed on a display unit for the calculation of the irradiation plan.

The presentation of the course over time of the combined first time series and second time series can be a presentation of the individual images of the first time series and second time series over time acquired at different times. A synchronization of the first time series and second time series can be advantageous for the presentation of the course over time of the first time series and second time series.

The course over time of the first time series can be presented in addition to the course over time of the second time series, or be presented overlaid on the course over time of the second time series. The course over time of the first time series and second time series can be visualized, for example, in a loop presentation, also called a movie-loop. In specific applications it is also possible for just the course over time of spatial regions of the first time series and second time series, which exhibit great reciprocal differences before combining, to be presented. The course over time of the first time series and the second time series can be displayed for a user on a display unit. The display of the course over time of the combined first time series and second time series can advantageously be used for quality assurance purposes, since, for example, successful merging of the first time series and second time series can be ensured. In addition to the presentation of the course over time, quantitative comparative measurements can also be supplied that quantitatively document the success of combining of the first time series and second time series.

In another embodiment, a presentation, averaged over time, of the combined first time series and second time series is displayed on a display unit for the calculation of the irradiation plan.

For this purpose, the first time series and the second time series can first be temporally overlaid and then averaged over time. A three-dimensional data set therefore results from the combined first time series and second time series, in which data set, not a respiratory curve of the patient, but only a mean breathing position of the patient is important. The presentation of the first time series and second time series averaged over time can be drawn up, for example, by forming a maximum or mean signal intensity of the voxels of the first time series and second time series over time (also called t-MIP or t-average).

In an embodiment, when carrying out the planned irradiation of the patient, a third parameter, which characterizes the progress of the irradiation, is detected, wherein a connection is made between the third parameter and the first parameter and/or the second parameter, and the implementation of the planned irradiation of the patient is adjusted using the connection that has been made.

In this way the first parameter used for irradiation planning and second parameter can also be used for controlling the actual irradiation of the patient by the irradiation unit. The connection between the third parameter and the first parameter or the second parameter can be made by the use of the techniques already described for combining the first parameter and second parameter. The third parameter, which can characterize the movement of the patient during irradiation, can be detected by a component of the irradiation unit, for example a camera.

Within the scope of a gating technique or trigger technique, adjustment of the implementation of the planned irradiation can involve a limitation of the irradiation to a specific respiratory phase of the patient, for example a complete inhalation. Alternatively or additionally, adjustment of the implementation of the planned irradiation can be tracking settings of a collimator of the irradiation unit to the movement of the patient within the scope of a tracking technique. Adjustment of the implementation of the planned irradiation can enable improved consideration of the respiration of the patient during irradiation. The connection that has already been made between the first parameter and second parameter can be used to particular advantage here.

The inventive irradiation planning unit includes a first time series acquisition unit, a second time series acquisition unit, a first parameter acquisition unit, a second parameter acquisition unit, a combining unit and a calculation unit, wherein the irradiation planning unit is designed for carrying out an inventive method.

In this way the irradiation planning unit is designed for carrying out a method for planning irradiation of a patient. The first time series acquisition unit is designed for acquiring a first time series from computed tomography scan data of the patient. The second time series acquisition unit is designed for acquiring a second time series from magnetic resonance scan data of the patient. The first parameter acquisition unit is designed for acquiring a first parameter which characterizes the first time series. The second parameter acquisition unit is designed for acquiring a second parameter which characterizes the second time series. The combining unit is designed for combining the first time series and the second time series using the first parameter and the second parameter. The calculation unit is designed for calculating an irradiation plan using the combined first time series and second time series.

The components of the irradiation planning unit, namely the first time series acquisition unit, second time series acquisition unit, first parameter acquisition unit, second parameter acquisition unit, combining unit and calculation unit, can for the most part be designed in the form of software components. These components can also be partially implemented, in particular when particularly fast calculations are involved, in the form of software-assisted hardware components, for example FPGAs or the like. Similarly, the required interfaces can, for example when it is merely a matter of acquiring data from other software components, be designed as software interfaces. They can, however, also be designed as interfaces constructed in terms of hardware, which are controlled by appropriate software. Of course it is also conceivable for a plurality of said components to be implemented in a combined manner in the form of an individual software component or software-assisted hardware component.

The inventive system having a computed tomography scanner and a magnetic resonance scanner also has an inventive irradiation planning unit.

The computed tomography scanner and the magnetic resonance scanner are installed separately from each other and supply scan data that can be used by the irradiation planning unit for calculating the irradiation plan. The irradiation planning unit is designed to send control signals to the system and/or to receive and/or process control signals in order to carry out an inventive method. The irradiation planning unit can be integrated in the system. The irradiation planning unit can also be installed separately from the system. The irradiation planning unit can be connected to the system.

The first time series can be acquired from computed tomography scan data of the patient can by operation of the computed tomography device. The first time series can then be transferred to the irradiation planning unit for further processing. The irradiation planning unit can then acquire the first time series by operation of the first acquisition unit. The second time series can be acquired from magnetic resonance scan data of the patient by operation of the magnetic resonance device. The second time series can then be transferred to the irradiation planning unit for further processing. The irradiation planning unit can then acquire the second time series by operation of the first acquisition unit.

The inventive non-transitory data storage medium can be loaded directly into a memory of a programmable processor of the irradiation planning unit and has program code that cause the inventive method to be implemented when the program code is run in the processor of the irradiation planning unit. The inventive method can consequently be carried out quickly, robustly and in a way that can be repeated in an identical manner. The processor must have the components such as an appropriate main memory, an appropriate graphics card or an appropriate logic unit, so the respective method steps can be carried out efficiently. Examples of electronically readable data carriers are a DVD, magnetic tape or a USB stick, on which electronically readable control information, in particular software (cf. above), is stored.

The advantages of the inventive irradiation planning unit, the inventive system and the inventive computer program product essentially correspond to the advantages of the inventive method, which have been described above in detail. Features, advantages or alternative embodiments mentioned in this context are similarly applicable to the other aspects of the invention. The corresponding functional features of the method are formed by appropriate tangible modules, in particular by hardware modules.

DESCRIPTION OF THE PREFERRED EMBODIMENTS

Figure 1:
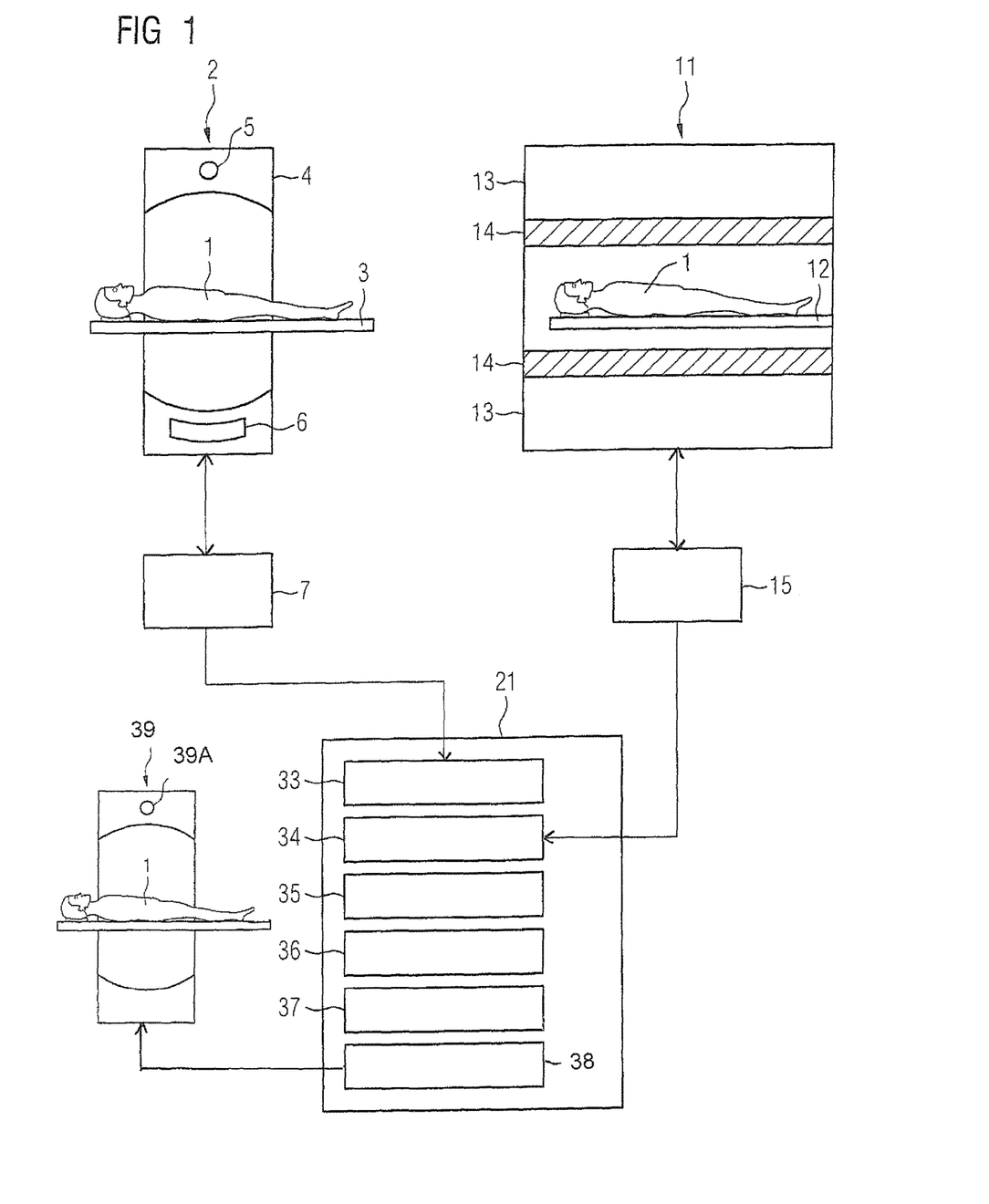
FIG. 1 is block diagram of an inventive system that has an inventive irradiation planning unit.

FIG. 1 illustrates an inventive system having a computed tomography scanner 2 and a magnetic resonance scanner 11, and an inventive irradiation planning unit 21.

The computed tomography scanner 2 has a gantry 4 that surrounds an acquisition region. At least one X-ray source 5 and at least one detector 6 are mounted so as to rotate around the acquisition region. The patient 1 can be positioned on a first patient positioning device 3 in the computed tomography scanner 2. The computed tomography scanner 2 has a first central computer 7 for controlling the computed tomography scanner 2. The illustrated computed tomography scanner 2 can of course have further components that computed tomography apparatuses conventionally have. The general mode of operation of a computed tomography apparatus is known to those skilled in the art, so a detailed description of the further components is not necessary herein.

The magnetic resonance scanner 11 has a magnetic unit 13 for generating a strong and constant main magnetic field. The magnetic resonance scanner 11 also has a coil unit 14 for generating magnetic field gradients and radio-frequency pulses. The coil unit 14 is also designed for receiving magnetic resonance signals, in particular from the patient 1. The patient 1 can be positioned in the magnetic resonance scanner 11 on a second patient positioning device 12. The magnetic resonance scanner 11 has a second central computer 15 for controlling the magnetic resonance scanner 11. The illustrated magnetic resonance scanner 11 can of course has further components that magnetic resonance apparatuses conventionally have. The general mode of operation of a magnetic resonance apparatus is known to those skilled in the art, so a detailed description of the further components is not necessary herein.

The illustrated system has an irradiation planning unit 21 which comprises a first time series acquisition unit 33, a second time series acquisition unit 34, a first parameter acquisition unit 35, a second parameter acquisition unit 36, a combining unit 37 and a calculation unit 38. Control signals corresponding to the calculated irradiation plan are provided to an irradiation unit 39 so as to administer the planned radiation therapy to the patient 1 including controlling the radiation source 39A of the irradiation unit 39. In this way the irradiation planning unit 21 is designed for carrying out a method as described in FIGS. 2-3.

For carrying out an inventive method the irradiation planning unit 21 loads the first time series and second time series from a database by means of the first time series acquisition unit 33, a second time series acquisition unit 34.

When the inventive method is carried out by the system and irradiation planning unit 21 combined, the first time series acquisition unit 33 of the irradiation planning unit 21 will acquire the first time series, which has been recorded by means of the computed tomography scanner 2. Furthermore, the second time series acquisition unit 34 of the irradiation planning unit 21 will acquire the second time series, which has been recorded by means of the magnetic resonance scanner 11. For this the irradiation planning unit 21 is connected to the first central computer 7 of the computed tomography scanner 2 and the second central computer 15 of the magnetic resonance scanner 11 with respect to data exchange.

Figure 2:
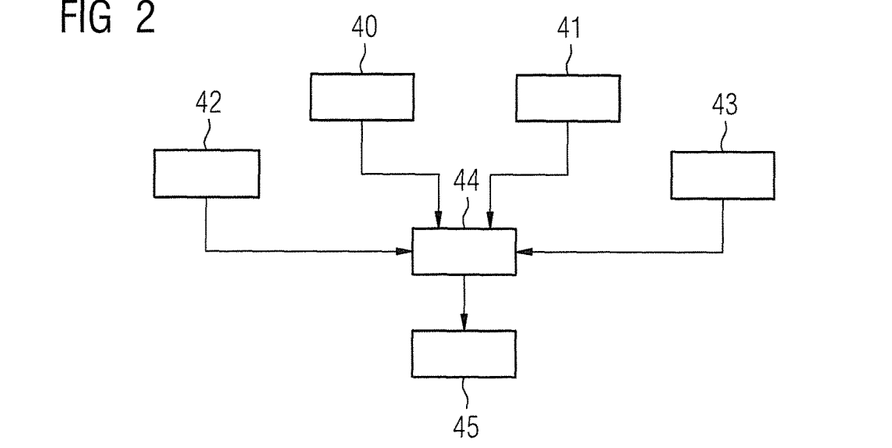
FIG. 2 shows a first embodiment of the inventive method.

FIG. 2 is a flowchart of a first embodiment of the inventive method for planning irradiation of a patient 1.

A first time series is acquired from computed tomography scan data of the patient by means of the first time series acquisition unit 33 in a first method step 40.

A second time series is acquired from magnetic resonance scan data of the patient by means of the second time series acquisition unit 34 in a further method step 41.

A first parameter, which characterizes the first time series, is acquired by means of the first parameter acquisition unit 35 in a further method step 42.

A second parameter, which characterizes the second time series, is acquired by means of the second parameter acquisition unit 36 in a further method step 43.

The first time series and the second time series are combined in a further method step 44 by means of the combining unit 37 using the first parameter and the second parameter.

An irradiation plan is calculated in a further method step 45 by means of the calculation unit 3 using the combined first time series and second time series.

Figure 3:
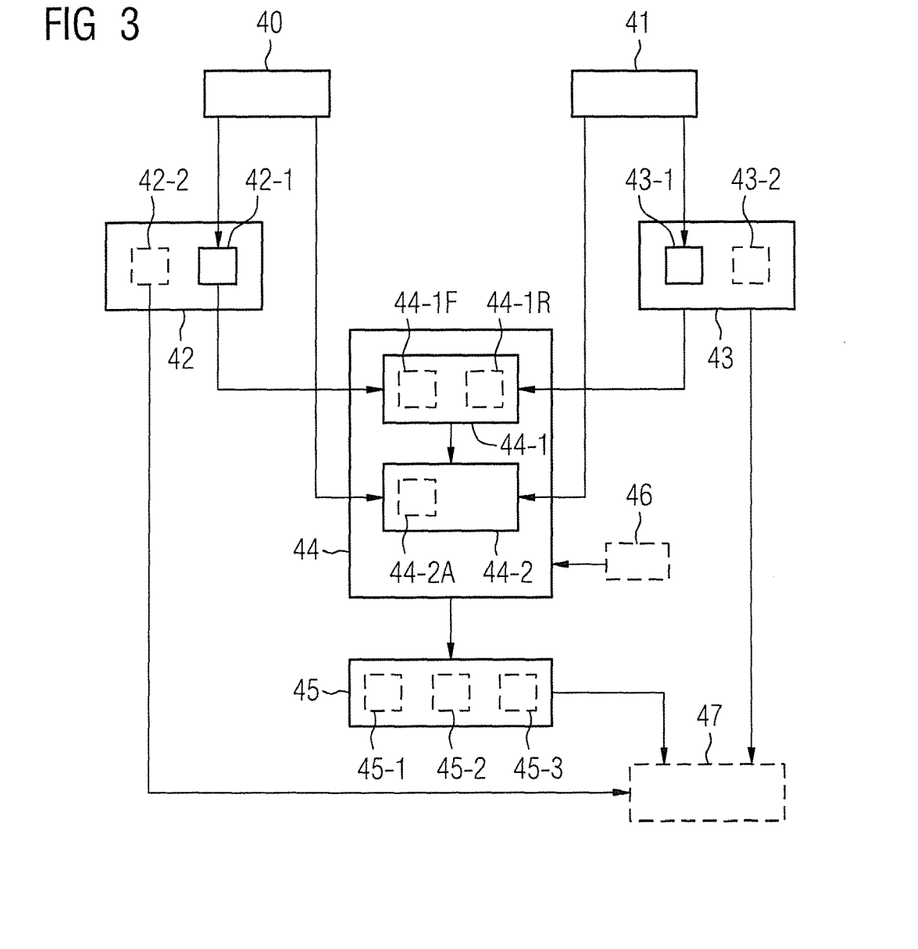
FIG. 3 shows a second embodiment of the inventive method.

FIG. 3 is a flowchart of a second embodiment of an inventive method for planning irradiation of a patient 1.

The following description is essentially limited to the differences from the exemplary embodiment in FIG. 2, with reference being made in respect of unvarying method steps to the description of the exemplary embodiment in FIG. 2. Method steps that essentially do not vary are basically numbered with the same reference numerals.

The embodiment of the inventive method shown in FIG. 3 essentially comprises method steps 40, 41, 42, 43, 44, 45 of the first embodiment of the inventive method according to FIG. 2. In addition, the embodiment of the inventive method shown in FIG. 3 comprises additional method steps and sub-steps. A sequence of the method alternative to FIG. 3, which has only some of the additional method steps and/or sub-steps illustrated in FIG. 3, is also conceivable. Of course a sequence of the method alternative to FIG. 3 can also have additional method steps and/or sub-steps.

In the case shown in FIG. 3 acquisition of the first parameter in further method step 42 includes determining a first vector field map from the first time series in a first substep 42-1 of further method step 42. Alternatively or additionally, acquisition of the first parameter can include the use of at least one of the following elements during acquisition of the time series of the computed tomography scan data in a second substep 42-2 of further method step 42:
   a respiratory belt placed on the patient 15,
   an optical camera,
   a spirometer,
   a radio-frequency-based movement detector,
   a marking element arranged with the patient 15.

In further method step 43 acquisition of the second parameter according to FIG. 3 includes determining a second vector field map from the second time series in a first substep 43-1 of further method step 43. Alternatively or additionally, acquisition of the second parameter can include the use of at least one of the following elements during acquisition of the time series of the magnetic resonance scan data in a second substep 43-2 of further method step 43:
   a magnetic resonance navigator scan which takes place at the same time as acquisition of the magnetic resonance scan data,
   a respiratory belt placed on the patient 15,
   a spirometer,
   a marking element arranged with the patient 15.

The first time series and second time series can therefore be combined in further method step 44 using the first vector field map and the second vector field map. For this the first parameter, in particular the first vector field map, and the second parameter, in particular the second vector field map, can be connected in a first substep 44-1 of further method step 44. The first time series and the second time series can be combined in a first sub-step 44-1F of merging of the first vector field map and the second vector field map over time. Alternatively or additionally, the first time series and the second time series can be combined by bringing the first vector field map and the second vector field map into spatial registration in a second sub-step 44-1R.

Once the first parameter, namely the first vector field map, and the second parameter, namely the second vector field map, have been connected, according to FIG. 3 combining the first time series and the second time series in a second substep 44-2 of further method step 44 includes a synchronization of the first time series and the second time series over a movement cycle of the patient 15. In a sub-step 44-2A of the second part step 44-2 the synchronization of the first time series and second time series can include an adjustment of a temporal arrangement of individual images of the first time series and/or second time series, with calculation of the irradiation plan including use of the adjusted temporal arrangement of the individual images of the first time series and/or second time series.

In a further method step 46 a rule, which describes a phase shift between the first parameter and the second parameter, can be loaded from a database, wherein the first time series and the second time series can then also be combined using the rule.

The first time series and second time series combined in further method step 44 can then be used in further method step 45 for irradiation planning by means of different possibilities. Some exemplary possibilities are illustrated in FIG. 3 as substeps 45-1, 45-2, 45-3 of further method step 45. Therefore, in a first substep 45-1 of further method step 45 the combined first time series and second time series can be used in a calculation of a dose distribution for the calculation of the irradiation plan. Alternatively or additionally, a presentation of a course over time of the combined first time series and second time series can be displayed on a display unit in a second substep 45-2 of further method step 45 for the calculation of the irradiation plan. Alternatively or additionally, a presentation, averaged over time, of the combined first time series and second time series can be displayed on a display unit in a third substep 45-3 of further method step 45 for the calculation of the irradiation plan.

Finally, it is also conceivable that in a further method step 47 a third parameter, which characterizes the progress of the irradiation, is acquired when carrying out the planned irradiation of the patient 15, wherein a connection is made between the third parameter and the first parameter and/or the second parameter, with the implementation of the planned irradiation of the patient being adjusted using the connection that has been made.

Figure 4:
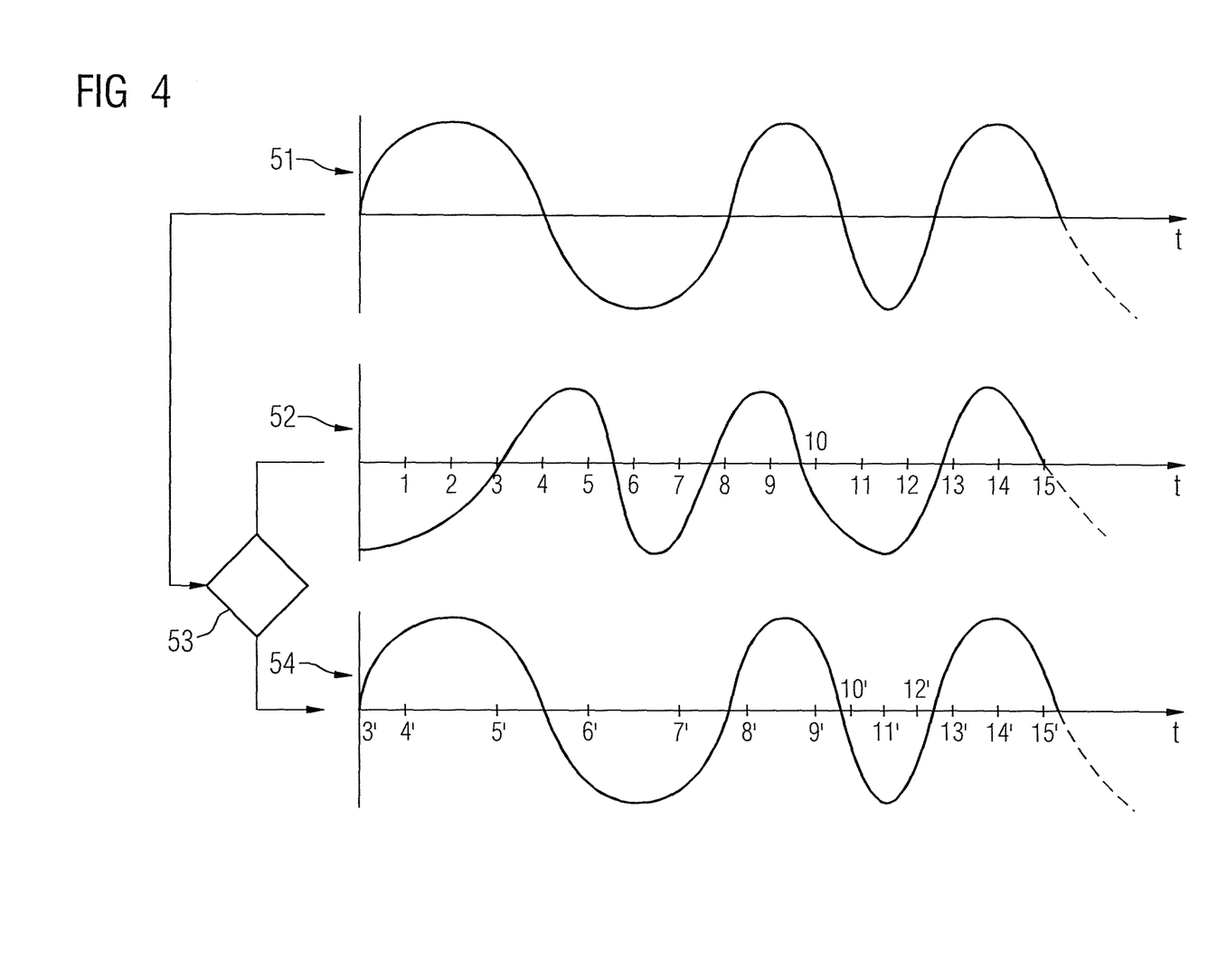
FIG. 4 schematically illustrates part of the inventive procedure.

FIG. 4 shows a schematic illustration of part of the inventive procedure. In FIG. 4 the movement of an exemplary point in the patient 15 is in each case plotted along a spatial coordinate over time t in three curves 51, 52, 54 one above the other, namely a first curve 51, a second curve 52 and a third curve 54. In each of the three curves 51, 52, 54 the vertical axis corresponds to the spatial coordinates and the horizontal axis to the course over time. The point whose temporal-spatial course is to be visualized in the curves 51, 52, 54 is localized at a location in the patient 15 that is sensitive to movement, for example in the liver of the patient 15.

The first curve 51 reproduces the course over time of the spatial coordinates of the point during acquisition of the first time series of the computed tomography scan data. It can be seen that the spatial coordinates of the point follow a cyclical movement of the patient 15, for example the respiratory movement. Therefore, maxima and minima of the spatial coordinates, which depend on a respiratory state of the patient 15, alternate over time during acquisition of the first time series.

The second curve 52 reproduces the temporal course of the spatial coordinates of the point during acquisition of the second time series of the magnetic resonance scan data. The spatial coordinates again follow the cyclical movement of the patient. The course over time of the spatial coordinates in the second curve 52 is phase-shifted compared to the course over time of the spatial coordinates of the first curve 51, however. Furthermore, there was obviously a different movement pattern of the patient 15, for example a different breathing pattern, during acquisition of the second time series than during acquisition of the first time series. The temporal sequence of the maxima and minima of the spatial coordinates is therefore developed differently in the second curve 52 to in the first curve 51.

In the example shown in FIG. 4, the acquisition of the second time series is a successive acquisition of 15 magnetic resonance individual images. The times at which the 15 magnetic resonance individual images are acquired are marked on the horizontal time axis of the second curve 52 by numbered graduation marks.

For irradiation planning, the second curve 52 should then be adjusted to the first curve 51 such that two temporally matching curve characteristics can result. This adjustment can take place in an adjustment step 53, which can correspond, for example, to further method step 43 in FIG. 2 or FIG. 3. The second curve 52 is adjusted to the first curve 51 in particular using the first parameter and second parameter, for example the first vector field map and the second vector field map.

The third curve 54 then shows the course over time of the spatial coordinates, adjusted to the respiratory cycle of the first time series, during acquisition of the second time series. As can be seen from FIG. 4, the third curve 54 is synchronized to the first curve 51. The synchronization occurred by a new temporal arrangement of the 15 magnetic resonance individual images of the second time series. The times at which the magnetic resonance individual images are arranged in the third curve 54 are again marked by graduation marks on the horizontal time axis of the third curve 54.

The 15 magnetic resonance individual images were arranged in such a way that the third curve 54 has an amplitude and a phase position adjusted to the first curve 51. For this a spacing of successive magnetic resonance individual images is partially increased and partially reduced in adjustment step 53. The first two magnetic resonance individual images from the second curve 52 are not contained in the third curve 54 either in the new temporal arrangement of the 15 magnetic resonance individual images.

The example in FIG. 4 is intended only for the purpose of illustration. Spatial and temporal units are randomly chosen here. The zero line of the spatial coordinates is also only randomly set. It is of course conversely conceivable for the course over time of the first time series to be adjusted to the course over time of the second time series. FIG. 4 again illustrates the example just one temporal adjustment of the time series. Of course a spatial adjustment of the image contents of the time series is alternatively or additionally conceivable. The temporal adjustment of the time series can also be made in a different manner to that shown in FIG. 4.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for planning radiation of a patient for radiation therapy, comprising:

providing a processor with a first time series acquired from computed tomography scan data of a patient;

providing said processor with a second time series acquired from magnetic resonance scan data of the patient;

in said processor, determining a first vector field map from said first time series that characterizes movement of the patient represented in said first time series;

in said processor, determining a second vector field map from said second time series that characterizes movement of the patient represented in said second time series;

in said processor, combining said first time series and said second time series by synchronizing said first time series and said second time series over a movement cycle of the patient, using said first vector field map and said second vector field map so as to obtain a combined vector field map that characterizes movement of the patient derived from said movement of the patient represented in said first time series and said movement of the patient represented in said second series;

in said processor, calculating an irradiation plan for irradiating the patient with a radiation source for radiation therapy, by using the combined vector field map to coordinate, in said irradiation plan, emission of radiation by said radiation source with said movement of the patient characterized in said combined vector field map; and in said processor, generating control signals corresponding to the calculated irradiation plan, and emitting said control signals to said radiation source so as to operate said radiation source according to said radiation plan, with said radiation emitted by said radiation source coordinated with said movement of the patient.

2. A method as claimed in claim 1 comprising synchronizing said first time series and said second time series by adjusting a temporal arrangement of individual images in at least one of said first time series and said second time series using said first vector field map and said second vector field map, and calculating said radiation plan using the adjusted temporal arrangement of the individual images of said at least one of said first time series and said second time series.

3. A method as claimed in claim 1 comprising combining said first time series and said second time series by mapping said first vector field map and said second vector field map over time.

4. A method as claimed in claim 1 comprising combining said first time series and said second time series bringing said first vector field map and said second vector field map into spatial registration with each other.

5. A method as claimed in claim 1 comprising combining said first time series and said second time series by calculating a dose distribution of radiation emitted by said radiation source for said radiation plan.

6. A method as claimed in claim 1 comprising visually presenting, at a display screen in communication with said processor, a course over time of said combined first time series and second time series.

7. A method as claimed in claim 1 comprising representing said radiation plan at a display screen in communication with said processor as a visual presentation averaged over time of the combined first time series and second time series.

8. A method as claimed in claim 1 comprising, when implementing said planned irradiation of the patient according to said irradiation plan, detecting a third parameter that characterizes progress of the irradiation and providing said third parameter to said processor and, in said processor, identifying a relationship between said third parameter and at least one of said first vector field map and said second vector field map, and adjusting implementation of the planned irradiation of the patient dependent on said relationship.

9. A system for planning irradiation of a patient for radiation therapy, comprising:

a computed tomography scanner;

a magnetic resonance scanner;

an irradiation unit comprising a radiation source;

a processor provided with a first time series acquired from a computed tomography scan of a patient implemented by said computed tomography scanner;

said processor also being with a second time series acquired from magnetic resonance scan of the patient implemented by said magnetic resonance scanner;

said processor being configured to determine a first vector map from said first time series that characterizes movement of the patient represented in said first time series;

said processor being configured to determine a second vector map from said second time series that characterizes movement of the patient represented in said second time series;

said processor being configured to combine said first time series and said second time series by synchronizing said first time series and said second time series over a movement cycle of the patient, using said first vector field map and said second vector field map so as to obtain a combined vector field map that characterizes movement of the patient derived from said movement of the patient represented in said first time series and said movement of the patient represented in said second series;

said processor being configured to calculate an irradiation plan for irradiating the patient with said radiation source for radiation therapy, by using the combined vector field map to coordinate, in said irradiation plan, emission of radiation by said radiation source with said movement of the patient characterized in said combined vector field map; and said processor being configured to generate control signals corresponding to the calculated irradiation plan, and to emit said control signals to said radiation source so as to operate said radiation source according to said radiation plan, with said radiation emitted by said radiation source coordinated with said movement of the patient.

10. A non-transitory, computer-readable data storage medium encoded with programming instructions, said storage medium being loaded into a computer for planning an irradiation plan of a patient for radiation therapy, said programming instructions causing said computer to:

receive a first time series acquired from computed tomography scan data of a patient;

receive a second time series acquired from magnetic resonance scan data of the patient;

determine a first vector map from said first time series that characterizes movement of the patient represented in said first time series;

determine a second vector map from said second time series that characterizes movement of the patient represented in said, second time series;

combine said first time series and said second time series by synchronizing said first time series and said second time series over a movement cycle of the patient, using said first vector field map and said second vector field map so as to obtain a combined vector field map that characterizes movement of the patient derived from said movement of the patient represented in said first time series and said movement of the patient represented in said second series;

calculate an irradiation plan for irradiating the patient for radiation therapy with said radiation source, by using the combined vector field map to coordinate, in said irradiation plan, emission of radiation by said radiation source with said movement of the patient characterized in said combined vector field map; and generate control signals corresponding to the calculated irradiation plan, and emit said control signals to said radiation source so as to operate said radiation source according to said radiation plan, with said radiation emitted by said radiation source coordinated with said movement of the patient.

* * * * *